United States Patent
Duckett, III et al.

(10) Patent No.: US 12,072,483 B2
(45) Date of Patent: Aug. 27, 2024

(54) METHOD FOR PRODUCING IMAGES FROM A MEDICAL DEVICE WITH SPLIT IMAGES ON COMMON IMAGE SENSORS

(71) Applicant: KARL STORZ Imaging, Inc., Goleta, CA (US)

(72) Inventors: George E. Duckett, III, Castaic, CA (US); Marios Kyperountas, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 18/097,679

(22) Filed: Jan. 17, 2023

(65) Prior Publication Data

US 2024/0069325 A1      Feb. 29, 2024

Related U.S. Application Data

(63) Continuation of application No. 17/116,976, filed on Dec. 9, 2020, now Pat. No. 11,586,029.

(51) Int. Cl.
*A61B 1/05*      (2006.01)
*A61B 1/00*      (2006.01)
(Continued)

(52) U.S. Cl.
CPC .... *G02B 23/2453* (2013.01); *A61B 1/000095* (2022.02); *A61B 1/00186* (2013.01);
(Continued)

(58) Field of Classification Search
CPC ............ A61B 1/00098; A61B 1/00186; A61B 1/00188; A61B 1/04
See application file for complete search history.

(56) References Cited

U.S. PATENT DOCUMENTS

| | | |
|---|---|---|
| 4,857,724 A | 8/1989 | Snoeren |
| 5,216,512 A | 6/1993 | Brujins et al. |

(Continued)

FOREIGN PATENT DOCUMENTS

| | | |
|---|---|---|
| EP | 0295728 A1 | 12/1988 |
| EP | 0469678 A1 | 2/1992 |

(Continued)

OTHER PUBLICATIONS

Marston, D. J., M. Vilela, J. Huh, J. Ren, M. L. Azoitei, G. Glekas, G. Danuser, J. Sondek, K. M. Hahn, "Multiplexed GTPase and GEF biosensor imaging enables network connectivity analysis," Nature Chemical Biology, Aug. 2020, pp. 826-833+, V. 16, Springer Nature, New York.

(Continued)

*Primary Examiner* — Aaron B Fairchild
(74) *Attorney, Agent, or Firm* — David N. Villalpando

(57) ABSTRACT

Methods are provided using light captured by an endoscope system. Substantially afocal light from the endoscope is manipulated and split. After passing through focusing optics, the already split light again split, this time in image space, producing four portions of light that may be manipulated relative to each other. The four portions of light are focused onto separate areas of two image sensors. The manipulation of the beams can take several forms, each offering distinct advantages over existing systems when individually displayed, analyzed and/or combined by an image processor.

20 Claims, 5 Drawing Sheets

(51) Int. Cl.
  *A61B 1/04* (2006.01)
  *G02B 23/24* (2006.01)
  *H04N 23/50* (2023.01)
(52) U.S. Cl.
  CPC ............ *A61B 1/00188* (2013.01); *A61B 1/04* (2013.01); *A61B 1/05* (2013.01); *H04N 23/555* (2023.01)

(56) References Cited

U.S. PATENT DOCUMENTS

| | | |
|---|---|---|
| 5,689,365 A | 11/1997 | Takahashi |
| 6,659,940 B2 | 12/2003 | Adler |
| 8,675,043 B2 | 3/2014 | Duparré et al. |
| 8,784,301 B2 | 7/2014 | McDowall |
| 8,988,539 B1 | 3/2015 | Pascoguin et al. |
| 9,510,739 B2 | 12/2016 | Adler |
| 2002/0057496 A1 | 5/2002 | Kanai |
| 2005/0200847 A1 | 9/2005 | Chen et al. |
| 2013/0038689 A1 | 2/2013 | McDowall |
| 2013/0041226 A1 | 2/2013 | McDowall |
| 2013/0235174 A1 | 9/2013 | Namii |
| 2015/0002646 A1 | 1/2015 | Namii |
| 2017/0351103 A1 | 12/2017 | Duckett et al. |
| 2019/0391383 A1 | 12/2019 | Duckett et al. |
| 2020/0107710 A1 | 4/2020 | Duckett et al. |
| 2020/0174244 A1 | 6/2020 | Duckett et al. |

FOREIGN PATENT DOCUMENTS

| | | |
|---|---|---|
| EP | 3049859 B1 | 4/2020 |
| JP | 2004313523 | 11/2004 |

OTHER PUBLICATIONS

Hamamatsu Photonics K.K., Dual camera image splitting optics done right, 2016, pp. 1-8, Hamamatsu Photonics, KK, Japan.

Kaiser, P., "Extended European Search Report," Apr. 11, 2022, pp. 1-6, European Patent Office, Munich.

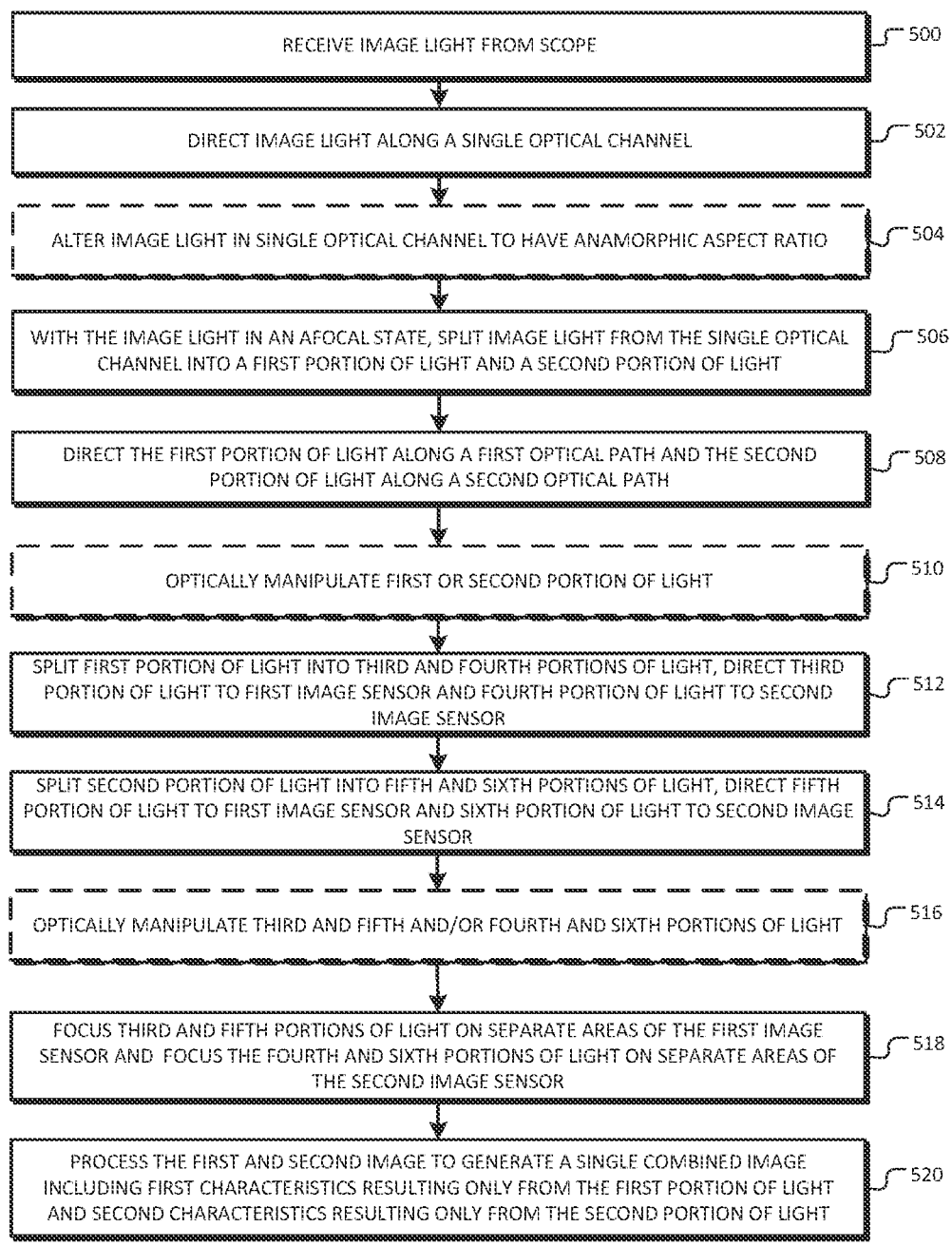

METHOD FOR PRODUCING IMAGES FROM A MEDICAL DEVICE WITH SPLIT IMAGES ON COMMON IMAGE SENSORS

CROSS-REFERENCE TO RELATED APPLICATION

This application is a continuation of U.S. patent application Ser. No. 17/116,976, filed on Dec. 9, 2020, and entitled "Medical Imaging Device with Split Image on Common Image Sensor," issued on Feb. 21, 2023, as U.S. Pat. No. 11,586,029 B2, the entire contents of the application and issued patent are incorporated herein by reference.

TECHNICAL FIELD OF THE INVENTION

The invention relates generally to the field of medical image capture and more specifically to endoscopic camera designs improved dual imaging.

BACKGROUND OF THE INVENTION

Dual image acquisition is a useful feature for endoscopic procedures wherein two video streams of the same scene are provided, but each video stream has different characteristics such as differing collected light spectra, different image focal planes or focal depths, or differing light intensities. In prior dual image systems, images have generally been collected, split in image space, and then focused onto two independent detectors. Such a configuration allows for some versatility, but is fairly expensive and complex, requiring an individual sensor and the associated electronics and mounting assemblies for each image acquired.

Some prior art systems do capture multiple images from a single imaging sensor chip, however these systems employ a beamsplitter placed in the image space of the camera. Such a design has significant limitations due to lack of flexibility in positioning any desired optical filters, lenses, or other elements in the optical paths downstream from the beamsplitter. Further, the cost associated with a dual imaging system may be higher than a conventional system due to duplication of certain optical components used in focusing and detecting the image light in each of the dual channels.

What is needed are devices and methods to enable an endoscopic camera to acquire dual images in a cost-effective manner. What is further needed are devices allowing the use of varied existing endoscopes for dual imaging applications, and the enablement of the detection of varied characteristics in the dual images.

SUMMARY OF THE INVENTION

It is an object of the invention to provide for improved endoscope acquisition of dual images and allow the use of varied existing endoscopes for dual imaging applications. It is a further object of the invention to allow detection of varied characteristics in the collected dual images, based on ability to vary the optical channels of the dual images. Enhanced depth of field, high dynamic range (HDR), Indocyanine Green (ICG) and other fluorescence analysis, and polarization studies all benefit from the collection of varying versions of the same image.

According to a first aspect of the invention, an optical imaging system is provided for use with a medical scope. The system includes a first optical group with a first beamsplitter, a second optical group, a second beamsplitter, one or more manipulating optical elements, and first and second image sensors. The first beamsplitter optically arranged in the first optical group to receive single optical image light in a substantially afocal state and split the single optical image light into a first portion of light directed along a first optical path and a second portion of light directed along a second optical path. The second optical group includes refractive elements optically arranged to receive the first and second portions of light from the first beamsplitter and focus them. The second beamsplitter is downstream from the second optical group arranged in an image space to split the first portion of light into a third and fourth portion of light and the second portion of light into a fifth and sixth portion of light. The third and fifth portions of light are focused onto a first and second area of the first image sensor, and the fourth and sixth portions of light are focused onto a first area and a second area of the second image sensor. The first and second areas of the first and second image sensor do not overlap. The one or more manipulating optical elements are positioned upstream of the second optical group to manipulate one or more of the single optical image light, the first portion of light, and the second portion of light.

According to some implementations of the first aspect, one or more of the manipulating optical elements is an element of the first optical group. In some implementations, the one or more of the manipulating optical elements include an anamorphic optical element in the first optical group, optically arranged to receive the single optical image light in an a substantially afocal state such that resulting images have an anamorphic aspect ratio. The manipulating optical elements may be prisms constructed to induce the anamorphic aspect ratio. In some implementations, the one or more of the manipulating optical elements is the first beamsplitter, and the first beamsplitter manipulates the first portion of light such that it has different optical characteristics from the second portion of light.

According to some implementations of the first aspect, the one or more manipulating optical elements include a spectral filter whereby spectral content of the first portion of light differs substantially from spectral content of the second portion of light. In some implementations, an image processor is included, programmed to process first and second images produced from the first and second image sensors, respectively, and generate there from a single image wherein the different spectral content of the first and second images are overlaid. The first portion of light may include infrared content while the second portion of light comprises visible light. In some implementations, the second beamsplitter includes a second spectral filter such that the third, fourth, fifth, and sixth portions of light have substantially different spectral content. An image processor may be included, programmed to process the first and second images and generating there from a single image with the infrared content and visible light content.

According to some implementations of the first aspect, the one or more manipulating optical elements comprises a means for manipulating light intensity of the first portion of light such that it has a different intensity than the second portion of light. According to some implementations of the first aspect, the second beamsplitter reflects a substantially different percentage of light than it transmits. With these implementations, an image processor may be included, programmed to process the first and second images to generate a single combined image with higher dynamic range than either the first or second image taken individually.

According to some implementations of the first aspect, the one or more manipulating optical elements include an optical element in the first optical path that is not present in the second optical path such that a first image produced with light from first optical path is brought to a different focus than a second image produced with light from the second optical path. According to some implementations of the first aspect, the first and second image sensors are in different focal planes. With these implementations, an image processor may be included, programmed to process the first and second images to generate a single image with an enhanced depth of field over either the first or second image taken individually.

According to some implementations of the first aspect, the one or more manipulating optical elements include a magnifier to manipulate the first portion of light such that first and second images produced with light from the first and second optical paths, respectively, have a different magnification at the image sensor. In some implementations, the second beamsplitter reflects a substantially different percentage of light than it transmits. With these implementations, an image processor may be included, programmed to process image data produced from the third, fourth, fifth, and sixth portions of light to generate a single combined image with higher dynamic range than that contained in any of the image data produced from the third, fourth, fifth, or sixth portions of light considered individually, the single combined image including spectral content based a plurality of the third, fourth, fifth and sixth portions of light.

According to some implementations of the first aspect, one or more of the manipulating optical elements is constructed to manipulate the first portion of light in a manner selected from the group: intensity manipulation, polarization manipulation, spectral manipulation, focal manipulation, and anamorphic aspect ratio manipulation. In some implementations, one or more of the manipulating optical elements is constructed to manipulate the second portion of light in a manner different from that manipulating the first portion of light and selected from the group: intensity manipulation, polarization manipulation, spectral manipulation, focal manipulation, and anamorphic aspect ratio manipulation.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein:

FIG. 5 is a flowchart of a method for producing endoscopy images according to an example embodiment.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective means that the lens group occupies a portion of the optical path that light travels (e.g., from the objective to the image sensor) for capturing images or video.

Because digital cameras, image sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
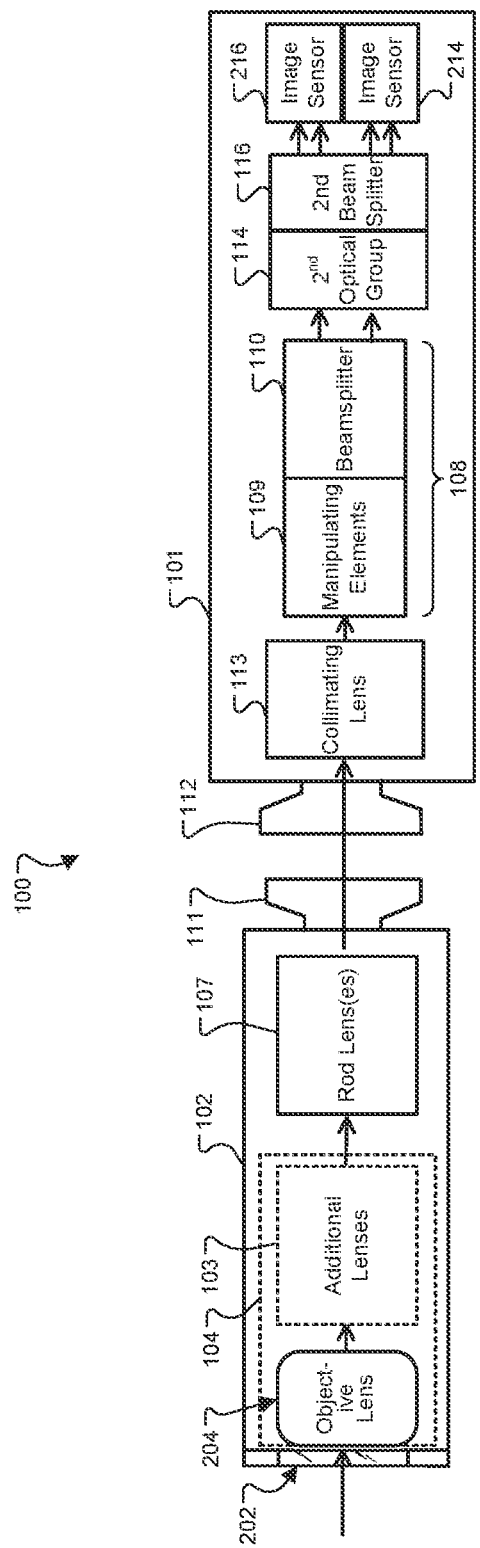
FIG. 1 is a block diagram of a medical imaging device 100 according to an example embodiment of the invention.

FIG. 1 is a block diagram of a medical imaging device 100 according to an example embodiment of the invention. Medical imaging device 100 ("device 100") includes a camera head 101 which may have an endoscope 102 attached via connectors 111 and 112. In some embodiments, an endoscope 102 and camera head 101 may be integrated into a single housing with no connectors needed. In some embodiments, the device 100 is provided as only the camera head 101 adapted to be connected to a suitable endoscope. Connectors 111 and 112 in this embodiment constitute what is generally called a "claw coupling" or dock-clutch coupling, comprising a clutch that couples two components, whereby at least one or both components are rotatable. Preferably, the claw (112) of the claw coupling is designed such that the eyepiece cup (111) is pushed towards the interface portion to engage the connection. When engaged the eyepiece cup and the interface portion rotate the same speed without slipping. However, the connectors 111 and 112 may be any suitable connector allowing light to pass from endoscope 102 to camera head 101. Various structural components supporting the depicted elements are omitted in the diagrams herein, as well as other components such as illumination lights sources and controls, which are known in the art and are not shown in order to avoid obscuring the relevant details of the example embodiments of the invention.

Camera head 101 includes a collimating lens 113 positioned at or behind a central window of connector 112 to receive and condition optical image light from the endoscope 102. Optically positioned in the optical channel after collimating lens 113 is a first substantially afocal optical group 108 including one or more manipulating optical elements 109 optically arranged to receive the optical image light and perform some type of optical manipulation, as further described below. By the term "substantially afocal," it is meant that the optical group as a whole does not have a significant focusing effect on the imaging light passing through and is not positioned in the image space of the optical system, and so does not receive focused image light. A beamsplitter 110 is optically arranged to receive the optical image light in a substantially afocal state from the endoscope 102 and split the optical image light into a first portion of light directed to a first optical path and a second portion of light directed to a second optical path as depicted by the two arrows showing the light path to second optical group 114. The first and second optical paths are further described with respect to the example embodiments below.

Second optical group 114 includes refractive elements optically arranged to receive the first and second portions of light from the beamsplitter 110 and focus them toward second beamsplitter 116, placed within the image space of the optical system. The second optical group 114 may also include further optical manipulating elements. The second beamsplitter 116 further splits the incoming two portions of light into four portions of light directed toward distinct areas of first and second image sensors 214 and 216. Second optical group 114 typically includes at least one focusing lens, with the group having a total positive power. Many suitable lenses and combinations of lenses may be used for second optical group 114. The sensor signal, containing two images, is processed as further described with respect to FIG. 6 and FIG. 8 to provide a combined image.

In some embodiments, system 100 includes an endoscope 102 as depicted at the left of the block diagram. The depicted endoscope is an example only, and many endoscope designs are suitable, including rigid and flexible endoscopes. Endoscope 102 includes a cover glass 202 at its distal tip, which in this version faces directly along the longitudinal axis of the endoscope 102, but may also be positioned at an angle relative to the longitudinal axis as is known in the art. Behind, or on the proximal side of, the cover glass 202 is shown a preferred position for the objective lens 204, set against or very near cover glass 202 and preferably assembled together with the cover glass in construction. While a wide-angle lens is preferred for objective lens 204, this is not limiting, and any suitable lens may be used in various embodiments. Objective lens 204 may be part of an objective lens group 104 which may include one or more additional lenses 103. The particular number and arrangement of lenses in the endoscope 102 will vary widely depending on the application. Optically arranged or attached at the proximal side of objective lens 204 or objective lens group 104 is a series of one or more rod lenses 107, which serve to pass the light down endoscope 102 in the proximal direction. Typically, several rod lenses 107 are employed, which may be separated by spacers or other lenses in any suitable manner known in the art. While the endoscope 102 may be of rigid design, shaft design variations are also known to allow rod lenses to be used in a semi-flexible shaft in which flexible joints are present in one or more places along the shaft between the rod lenses, while the shaft is rigid along the portions containing a rod lens. Such a shaft design may be used in various embodiments of the invention.

Figure 2:
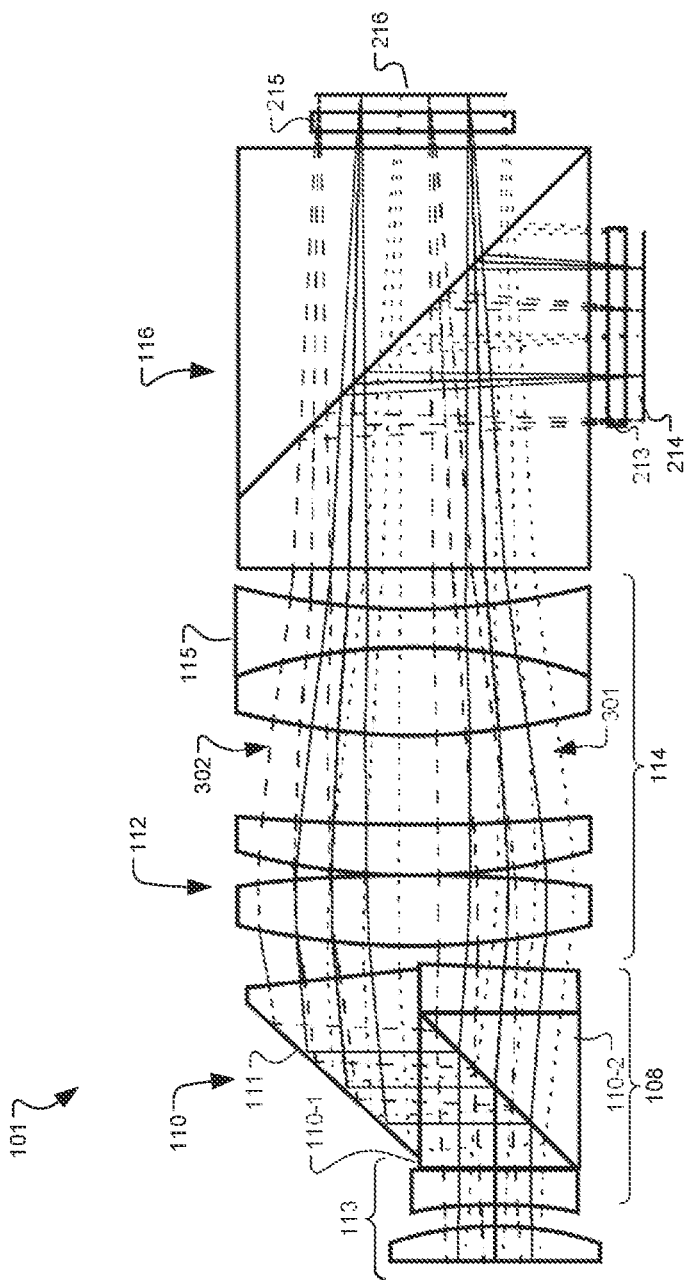
FIG. 2 is a partial cross section diagram of a camera head 101 showing the optical assembly construction according to an example embodiment.

FIG. 2 is a partial cross section diagram of a camera head 101 showing the optical assembly construction according to an example embodiment. The cross section includes a light ray diagram showing the passage of image light through the assembly to image sensors 214 and 216. The depicted optical elements are in diagram form only and are not drawn to scale. The depicted optical assembly may be employed with endoscope devices and systems having an integrated camera or an external detachable camera head. As shown, the optical assembly starts at collimating lenses 113 where the image light enters the camera head. Collimating lenses 113 may have a slightly positive or negative power in order to adjust the image light to the desired condition to be received by first optical group 108, preferably with light rays close to parallel. First optical group 108 in this version a includes a first beamsplitter 110 optically arranged to receive single optical image light in a substantially afocal state and split the single optical image light into a first portion of light 301 directed along a first optical path and a second portion of light 302 directed along a second optical path. In this embodiment, beamsplitter 110 is constructed of prisms, including the lower right angle prisms 110-1 and 110-2 with a suitable partially reflective coating along their adjacent surface, by which the image light is split with a first portion passing through along first optical path 301 and a second portion reflected upward along second optical path 302 as depicted. Adjacent to the beamsplitter 110 is an upper prism 111 that reflects light along the second optical path 302 as depicted. As discussed above, the first and second portions of light may include different spectral content.

Optically arranged downstream of first optical group 108 is a second optical group 114 including refractive elements optically arranged to receive the first and second portions of light from the first beamsplitter and focus them. In this embodiment, second optical group 114 includes a lens pair 112 having a total positive power to focus and align the first and second portions of light along first and second optical paths 301 and 302. A second lens pair 115 is optically arranged downstream of lens pair 112, including a biconvex lens with a positive power followed by a bi-concave lens with a negative power to align first and second optical paths 301 and 302 with a second beamsplitter 116. As can be understood from the ray diagram, lens pair 115 and the rest of second optical group 114 are preferably symmetrically arranged with respect to the first and second optical paths 301 and 302, and large enough to span both paths. That is, second optical group 114 is positioned with the axis pointing between the first and second paths such that each path has similar incidence on lens 115, symmetrical about the central axis of group 114.

A second beamsplitter 116 is positioned downstream from the second optical group and arranged to split the first portion of light 301 into a third and fourth portion of light and the second portion of light 302 into a fifth and sixth portion of light, as can be seen in the light ray diagram with the respective portions of light directed to first and second image sensors 214 and 216.

The third and fifth portions of light are focused onto a first and second area of first image sensor 214, and the fourth and sixth portions of light are focused onto a first area and a second area of second image sensor 216. As can be seen, the first and second areas of the first and second image sensors do not overlap. First image sensor 214 is positioned downstream of a cover glass or protective layer 213, with the image sensor lying parallel the longitudinal axis of camera head 101, while second image sensor 216 is positioned downstream of a cover glass or protective layer 215, with the image sensor standing perpendicularly the longitudinal axis.

In some embodiments, one or more manipulating optical elements are positioned upstream of second optical group 114 to manipulate one or more of the single optical image light, first portion of light 301, or second portion of light 302. The one or more of the manipulating optical elements may be an element of the first optical group, such as an anamorphic optical element optically arranged to receive the single optical image light in a substantially afocal state such that resulting images have an anamorphic aspect ratio. The anamorphic optical element may include one or more lenses constructed to induce the anamorphic aspect ratio. The manipulating optical element may be first beamsplitter 110.

For example, first beamsplitter 110 may manipulate the incoming light such that the first portion of light 301 has different optical characteristics from second portion of light 302.

In some embodiments, the one or more manipulating optical elements include a spectral filter whereby spectral content of first portion of light 301 differs substantially from spectral content of the second portion of light 302. For example, first portion of light 301 may include infrared content with second portion of light 302 including visible light. Second beamsplitter 116 may include a second spectral filter such that the third, fourth, fifth, and sixth portions of light have substantially different spectral content.

In some embodiments, the one or more manipulating optical elements include an intensity filter for manipulating light intensity of first portion of light 301 such that it has a different intensity than second portion of light 302. Second beamsplitter 116 may be constructed to reflect a substantially different percentage of light to first image sensor 214 than it transmits to second image sensor 216.

In some embodiments, the one or more manipulating optical elements include an optical element in the first optical path that is not present in the second optical path such that a first image produced with light from first optical path is brought to a different focus than a second image produced with light from the second optical path. The first and second image sensors may be in slightly different focal planes to accommodate for different focal lengths in the optical paths.

In some embodiments, the one or more manipulating optical elements comprises a magnifier to manipulate the first portion of light such that first and second images produced with light from the first and second optical paths, respectively, have a different magnification at the image sensor.

The second optical group 114 includes refractive elements optically arranged in both the first and second optical paths to receive the first and second portions of light from the beamsplitter 110 and focus the first portion as a first image onto a first area of a common image sensor 216 and the focus second portion as a second image onto a second area the common image sensor 216, different from the first area Further, while lenses 112 and 115 in this embodiment focus and direct both portions of light, other versions may include one or more lenses that perform focusing or diverging operations on only a single one of the optical paths. For example, lens 112 and/or 115 might be replaced with a separate focusing lens for each path.

Figure 3:
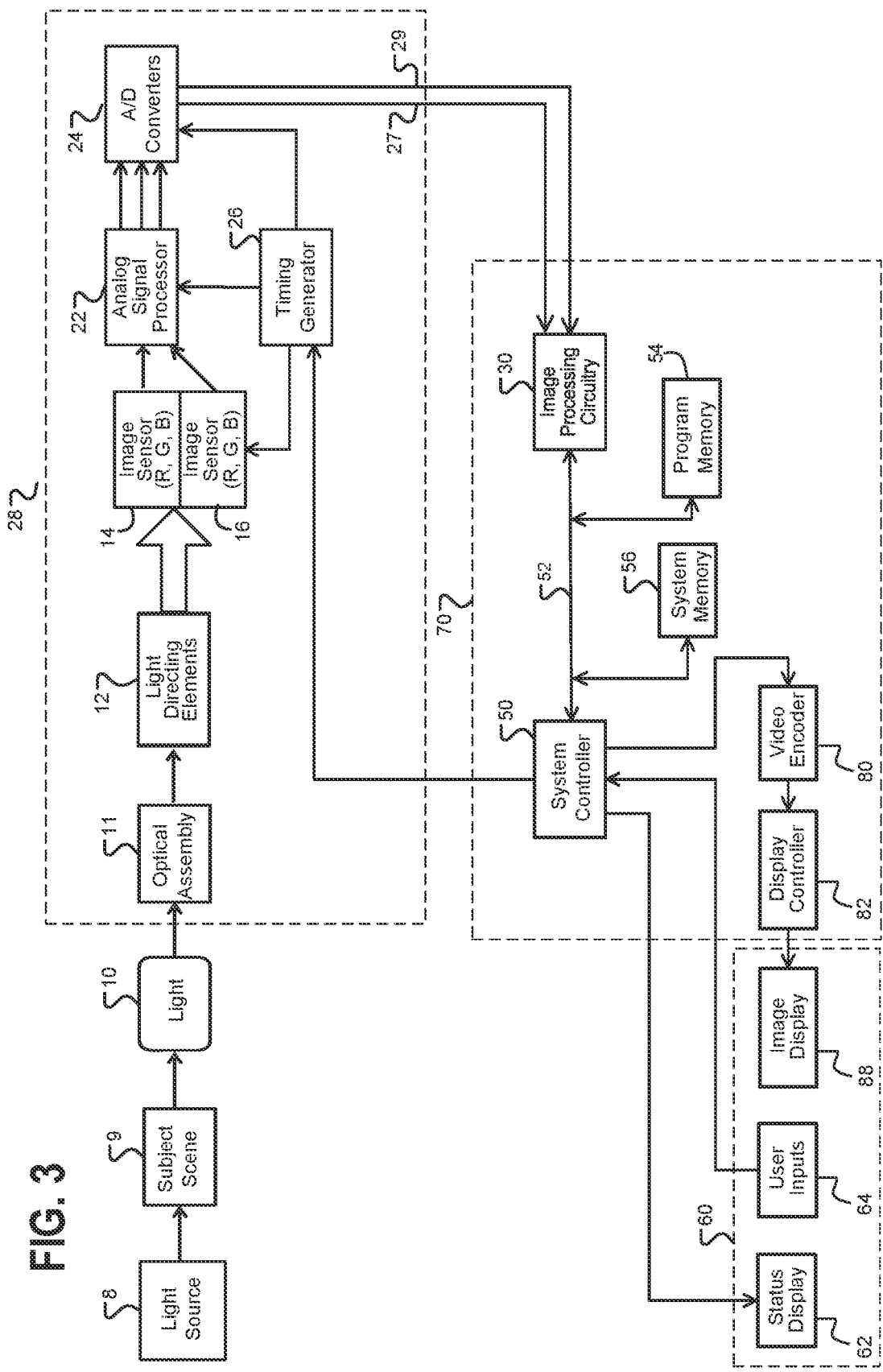
FIG. 3 is a hardware block diagram of system including an example image capture device according to an example embodiment of the invention.

FIG. 3 is a block diagram of an optical instrument system according to an example embodiment of the present invention. While this example circuit is shown for an endoscope, the present invention is applicable to other instruments such as borescopes, or exoscopes, for example.

A light source 8 illuminates subject scene 9 and light 10 reflected from (or, alternatively, as in the case of certain fluorescent or digital microscope arrangements, transmitted or emitted by) the subject scene forms an optical image via an optical channel assembly 11, where the light passed to the camera head, typically using a relay system comprising rod lenses. At the camera head the light is focused, aligned with the scope axis or a desired optical axis, and passed to a distal side of optical channel assembly 11 where light directing elements 12 direct different portions of the light to form different portions of the image on first and second solid-state image sensors 14 and 16.

In this embodiment, optical channel assembly 11 includes an imaging system and may be constructed according to a variety of known methods. Image sensors 14 and 16 convert the incident light to an electrical signal by, for example, integrating charge for each picture element (pixel). The image sensors 14 and 16 may be active-pixel type complementary metal oxide semiconductor sensors (CMOS APS) or a charge-coupled devices (CCD), to give just two possible examples. The output analog signal from the image sensors is processed by analog signal processor 22 and applied to analog-to-digital (A/D) converter 24 for digitizing the analog sensor signals. In some versions (typically CMOS designs), the analog signal processing and A/D converters may be integrated into individual sensor models attached to each sensor 14 and 16.

The system's camera 28 generally includes timing generator 26, which produces various clocking signals to select rows and pixels and synchronizes the operation of image sensors 14 and 16, analog signal processor 22, and A/D converter 24. A camera head electronic assembly typically houses image sensors 14 and 16, while the locations of each of analog signal processor 22, the A/D converter 24, and the timing generator 26 may vary, for example in the scope handle 102. The non-optical, functional elements of the camera 28 may be fabricated as a single integrated circuit as is commonly done with CMOS image sensors or they may be separately-fabricated integrated circuits.

The system controller 50 controls the overall operation of the image capture device based on a software program stored in program memory 54. This memory can also be used to store user setting selections and other data to be preserved when the camera 28 is turned off. Data connections 27 and 29 carry the digital image data of image sensors 14 and 16, respectively, to image processing circuitry 30, which may be integrated with system controller 50 in some versions or may be a separate programmable logic device or data processor. A data bus 52 provides a pathway for address, data, and control signals. In some variations, data bus 52 may also carry data connections 27 and 29.

Image processing circuitry 30 performs image processing operations including the operations to combine two images from image sensors 14 and 16 as necessary, including processing the sub-images based on the third, fourth, fifth, and sixth portions of light. Image processing circuitry 30 is programmed to process image data produced from a plurality of the third, fourth, fifth, and sixth portions of light, and, in some embodiments, to generate a single combined image including image data produced from the third, fourth, fifth, or sixth portions of light. In some embodiments, the combined image has higher dynamic range than that contained in any of the image data produced from the third, fourth, fifth, or sixth portions of light considered individually. In some embodiments, the combined image has an enhanced depth of field over that of image data from the first and second image sensors individually.

Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays may be used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g., on image display 88). The GUI typically includes menus for making various option selections.

Image processing circuitry 30, system controller 50, system and program memories 56 and 54, video encoder 80, and display controller 82 may be housed within camera control unit (CCU) 70. CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

Figure 4B:
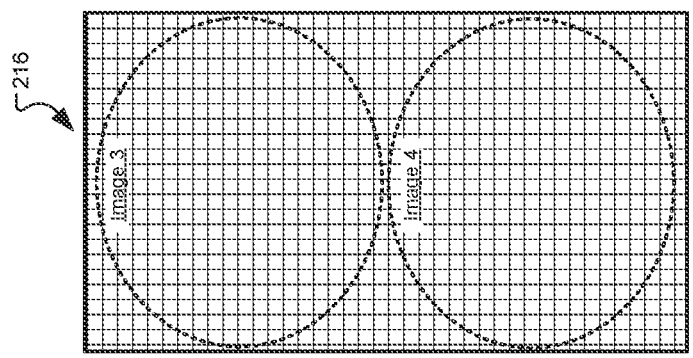
FIG. 4B depicts various portions of image light focused on first and second image sensors.
Figure 4B:
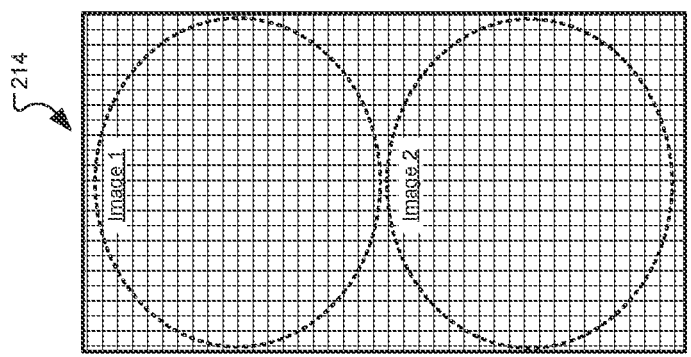
Figure 4A:
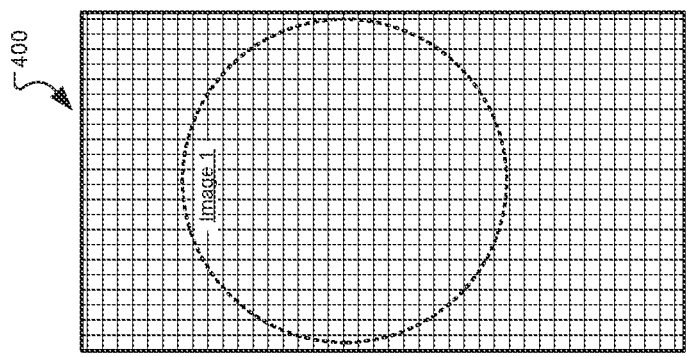
FIG. 4A is a diagram representing image light focused on an image sensor according to the prior art to capture image data for a single image.

FIG. 4A is a diagram representing image light focused on an image sensor 400 according to the prior art to capture image data for a single image labeled Image 1. Sensor 400 illustrates the sensing area of the image sensor with light-sensitive pixels shown as a grid. FIG. 4B depicts various portions of image light focused on first and second image sensors according to some embodiments. As depicted, the third and fifth portions of light are focused on first image sensor 214, forming Images labeled Image 1 and Image 2, and the fourth and sixth portions of light are focused on second image sensor 216 forming images labeled Image 3 and Image 4. In this diagram images 1, 2, 3, and 4 exhibit an anamorphic aspect ratio, representing embodiments where the incoming light, in most cases, is manipulated to achieve this aspect ratio, in order to maximize the number of pixels of the sensors receiving useable image information. Image processing is then used to conform the displayed image back to the proper aspect ratio.

FIG. 5 is a flowchart of a method for producing endoscopy images according to an example embodiment. The method may be performed employing any of the various example embodiments of endoscope and camera head devices as described herein, with a suitable camera control unit such as that described above to process the image data. The method begins at process block 500 where it includes receiving the image light from an endoscope. The endoscope device used may be a separate device attached to a camera head or an endoscope integrated with a camera head. At process block 502, the process directs the received image light along a single optical channel. At block 504, the process alters the image light, still in a single optical channel, to have an anamorphic aspect ratio. The final anamorphic ratio is designed to allow improved use of image sensor area when the image light is directed at the sensor. Some embodiments may not include block 504 as indicated by the dotted lines. Next at process block 506, with the image light in a substantially afocal state, the process includes splitting the image light from the single optical channel into a first portion of light and a second portion of light. Then at block 508, the process directs the first portion of light along a first optical path and the second portion of light along a second optical path. Directing the light is preferably done with a first beamsplitter such as the example splitters described herein.

Next at process block 510 the process includes optically manipulating the first or second portions of light relative to each other. As described above, the optical manipulation at this block may include one of manipulating the spectrum of the light, manipulating the intensity of the light, manipulating the focus of the light, manipulating the depth of field of the optical path, manipulating the polarization of one beam relative to the other, magnifying or applying an optical filter of some type.

Then at process block 512, the process includes splitting the first portion of light into a third and fourth portion of light and then directing the third portion of light to a first image sensor and directing the fourth portion of light to the second image sensor. As described above, the splitting is typically accomplished with a second beamsplitter. While in the diagram the splitting is shown separately from the optical manipulation at block 516, these functions may be accomplished separately or simultaneously (such as with a beamsplitter that manipulates one emerging beam relative to the other while splitting). At block 514, the process splits the second portion of light into fifth and sixth portions of light and directs the fifth portion of light to the first image sensor and the sixth portion of light to the second image sensor. In some embodiments, this splitting is performed by the second beamsplitter employed at block 512, while in other embodiments a separate beamsplitter is used for the second portion of light.

At block 516, the process includes optically manipulating the two portions of light directed to one of the image sensors, either the third and fifth portions of light and/or the fourth and sixth portions of light. The optical manipulation may include the various options listed with respect to block 510 and is typically selected to compliment the manipulation performed at block 510. For example, block 510 may perform a spectral filter to separate fluoresced light, while block 516 may adjust the intensity of light to provide low intensity image data based on the third and fifth portions of light and high intensity image data based on the fourth and sixth portions of light. This combination enables the use of fluoresced imaging along with HDR imaging. As another example, block 510 may adjust the focal depth of one of the first and second portions of light, while block 516 adjusts the light intensity. Preferably, such a focal depth adjustment is accomplished by offsetting the focal plane of one sensor. This combination enables imaging with a high depth-of-field along with HDR imaging.

At block 518, the process focuses the third and fifth portions of light on separate areas of the first image sensor and focuses the fourth and sixth portions of light on separate areas of the second image sensor. Next at block 520, image processing is performed on the image data from the first and second image sensors. In some embodiments, the image processing is applied to image data based on the third, fourth, fifth, and sixth portions of light to generate a single combined image including first characteristics resulting only from the third and fifth portions of light (from the first image sensor) and second characteristics resulting only from the fourth and sixth portions of light (from the second image sensor). In other embodiments, the process creates two images based on the image data from two or more of the portions of light. The processing is performed by a CCU such as the CCU 70 of FIG. 3, or other suitable image processing circuitry.

The image characteristics from the different portions of light may be designed to be any of a number of characteristics desired to be measured through the endoscope. For example, in some versions the spectral content of the first portion of light differs substantially from the spectral content of the second portion of light. The first portion of light may include infrared content with the second portion of light including visible light, for example. A combined image based on such a scheme may use designated colors to show the infrared content superimposed on the visible light content in a manner known in the art. In another embodiment, the first portion of light has a different intensity range than the second portion. This may be accomplished by reflective characteristics of the beamsplitter, or by a filter or filters or other suitable optical element or elements placed in one or both of first and second optical paths. Processing the image data with different intensity ranges provide a high dynamic range (HDR) single combined image with higher dynamic range than either the first or second image taken individually. The HDR imagery may further enhanced by also performing optical manipulation to the intensity at the second manipulation step, resulting in four images of the same scene of varying intensity. In another example embodiment, the process includes focusing the first image on the common image sensor differently than focusing the second image. The image processing of block 912 may extract features that are in sharper focus in one of the two images, or, as with the varying intensity value, four such focal positions may be captured and combined. Such an embodiment results in a single image with a larger depth of field than either the first or second image taken individually. Still other of the many possible embodiments may place a polarized filter within the beamsplitter or in the first and second optical paths, allowing the dual images to each acquire light with a different polarization. Known image processing techniques for polarization studies may be applied in processing the dual images from such an embodiment. And of course, any of the first manipulations discussed above may be combined with a second manipulation of a different type; for example, a first manipulation by intensity, and a second manipulation by spectrum is only one of the many possible combinations all represented by the present invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An imaging method for producing images from a medical scope, comprising the steps of:
   receiving, in a substantially afocal state, an image light from a medical scope;
   directing the received image light along a single optical channel;
   splitting the received image light into a substantially afocal first portion of light and a substantially afocal second portion of light;
   directing the first portion of light along a first optical path and the second portion of light along a second optical path;
   passing the first portion of light and the second portion of light through focusing optics such that they come into focus at an image plane of a first image sensor or an image plane of a second image sensor;
   splitting, in an image space, the first portion of light after passing through the focusing optics into a third focused portion and a fourth focused portion of light and directing the third focused portion of light to a first portion of the first image sensor and the fourth portion of light to a second portion of the second image sensor;
   splitting, in an image space, the second portion of light after passing through the focusing optics into a fifth focused portion of light and a sixth focused portion of light and directing the fifth portion of light to a second portion of the first image sensor and the sixth portion of light to a second portion of the second image sensor, wherein the first and second portions of both the first and second image sensors do not overlap;
   capturing an image of the third focused portion of light and the fourth focused portion of light with the first image sensor; and
   capturing an image of the fifth focused portion of light and the sixth focused portion of light with the second image sensor.

2. The imaging method of claim 1, comprising the further step of optically manipulating the received image light.

3. The imaging method of claim 2, wherein the step of optically manipulating the received image light includes altering the image light such that it has an anamorphic aspect ratio.

4. The imaging method of claim 1, comprising the further step of manipulating the first or second portions of light relative the other.

5. The imaging method of claim 4, wherein the step of manipulating the first or second portions of light relative to the other occurs during the step of splitting the received image light.

6. The imaging method of claim 5, wherein the step of manipulating the first or second portions of light relative to each other results in the first and second portions of light having different spectral content from each other.

7. The imaging method of claim 4, wherein the step of manipulating the first or second portions of light relative to each other results in the first and second portions of light having different spectral content from each other.

8. The imaging method of claim 4, wherein the step of manipulating the first or second portions of light relative to each other results in the first and second portions of light having different polarizations.

9. The imaging method of claim 4, wherein the step of manipulating the first or second portions of light relative to each other results in the first and second portions of light having different focal planes.

10. The imaging method of claim 4, wherein the step of manipulating the first or second portions of light relative to each other results in the first and second portions of light having different intensity values.

11. The imaging method of claim 4, wherein the step of manipulating the first or second portions of light relative to each other results in the first and second portions of light having different magnifications.

12. The imaging method of claim 4, wherein the step of splitting the first portion of light after passing through the focusing optics further comprises manipulating the third focused portion of light relative to the fourth focused portion of light.

13. The imaging method of claim 12, wherein the step of splitting the second portion of light after passing through the focusing optics comprises manipulating the fifth focused portion of light relative to the sixth focused portion of light.

14. The imaging method of claim 12, wherein the third focused portion of light and the fourth focused portion of light are manipulated such that they have different spectral content from each other.

15. The imaging method of claim 12, wherein the third focused portion of light and the focused fourth portion of light are manipulated such that they have a different polarization from each other.

16. The imaging method of claim 12, wherein the third focused portion of light and the fourth focused portion of light are manipulated such that they have different intensity values.

17. The imaging method of claim 1, wherein the step of passing the first and second portions of light through focusing optics comprises passing both first and second portions of light through the same focusing optics.

18. The imaging method of claim 1, wherein the step of receiving an image light from a medical scope further comprises the step of collimating the received image light.

19. The imaging method of claim 1, comprising the further step of processing the captured first image and the captured second image.

20. The imaging method of claim 19, wherein the step of processing the captured first image and the captured second image comprises the step of generating therefrom a resultant image, the resultant image being a combination of at least portions of three or more of captured image data from the first and second portions of the first and second image sensors.

* * * * *